(12) United States Patent
Locati et al.

(10) Patent No.: US 11,957,866 B2
(45) Date of Patent: *Apr. 16, 2024

(54) BLINDING CAP FOR NEEDLE SHIELD AND RELATED SYRINGE ASSEMBLY

(71) Applicant: Fisher Clinical Services GmbH, Allschwil (CH)

(72) Inventors: Patrick Locati, Ettingen (CH); Guido Hunkeler, Schonenbuch (CH); Alain Duerr, Basel (CH)

(73) Assignee: Fisher Clinical Services GmbH, Allschwil (CH)

( * ) Notice: Subject to any disclaimer, the term of this patent is extended or adjusted under 35 U.S.C. 154(b) by 352 days.

This patent is subject to a terminal disclaimer.

(21) Appl. No.: 17/354,435

(22) Filed: Jun. 22, 2021

(65) Prior Publication Data

US 2021/0308363 A1    Oct. 7, 2021

Related U.S. Application Data

(63) Continuation of application No. 16/261,200, filed on Jan. 29, 2019, now Pat. No. 11,077,242.

(60) Provisional application No. 62/627,418, filed on Feb. 7, 2018.

(51) Int. Cl.
  *A61M 5/32* (2006.01)
  *A61M 5/00* (2006.01)
  *A61M 5/28* (2006.01)

(52) U.S. Cl.
  CPC .............. *A61M 5/002* (2013.01); *A61M 5/28* (2013.01); *A61M 5/3202* (2013.01); *A61M 5/3204* (2013.01); *A61M 2207/00* (2013.01)

(58) Field of Classification Search
  CPC .......................... A61M 5/3202; A61M 5/3204
  See application file for complete search history.

(56) References Cited

U.S. PATENT DOCUMENTS

| | | | |
|---|---|---|---|
| 8,998,855 B2 | 4/2015 | Hudson et al. | |
| 9,545,480 B2 | 1/2017 | Hunkeler et al. | |
| 11,077,242 B2* | 8/2021 | Locati ..................... | A61M 5/28 |
| 2012/0238961 A1 | 9/2012 | Julian | |
| 2013/0204197 A1 | 8/2013 | Bicknell et al. | |
| 2013/0281938 A1 | 10/2013 | Ekman et al. | |
| 2015/0238704 A1 | 8/2015 | Evans et al. | |
| 2016/0144122 A1 | 5/2016 | Locati et al. | |

OTHER PUBLICATIONS

European Search Report dated Jul. 15, 2019, issued in European Application No. 19155429.4, filed Apr. 9, 2019.

* cited by examiner

*Primary Examiner* — Deanna K Hall

(74) *Attorney, Agent, or Firm* — Michael Best & Friedrich LLP

(57) ABSTRACT

A blinding cap for covering a needle shield that is covering a needle of a syringe includes an elongated body extending between a proximal end and an opposing distal end, the body at least partially bounding a chamber. An annular sleeve projects from the proximal end of the body and at least partially bounds a channel. A first flange radially inwardly projects from the body into the chamber, the first flange at least partially bounding an opening that provides communication between the chamber and the channel.

24 Claims, 14 Drawing Sheets

BLINDING CAP FOR NEEDLE SHIELD AND RELATED SYRINGE ASSEMBLY

CROSS-REFERENCE TO RELATED APPLICATIONS

This application is a continuation of U.S. application Ser. No. 16/261,200, filed Jan. 29, 2019, which claims the benefit of Provisional Application No. 62/627,418, filed Feb. 7, 2018, which are incorporated herein by specific reference.

BACKGROUND OF THE INVENTION

1. The Field of the Invention

The present invention relates to blinding caps used to cover rigid needle shields and to syringe assemblies that incorporate such blinding caps.

2. The Relevant Technology

Clinical trials for some pharmaceutical drugs require that the drug dosage and corresponding placebo dosage be delivered in a blinded study through the use of pre-filled syringes. Each syringe comprises a syringe barrel that houses the dosage, a needle projecting from the syringe barrel, and a plunger rod with correspond stopper that is used to dispense the dosage out of the syringe barrel through the needle. For safety reasons, a rigid needle shield is removable attached to the syringe barrel and covers the needle when the syringe is not in use. At the time of injection, the rigid needle shield is simply pulled off of the syringe barrel to expose the needle.

As part of the protocols for the blinded study, a plurality of syringes are each preloaded with a single dose of the drug, comparator or placebo prior to shipping for use. The syringe barrels are typically blacked out so that the recipient and person delivering the dosage are blind as to any visual properties of the dosage. This is particularly helpful in avoiding any perceived distinctions between the drug and either the comparator, the placebo or both.

Although blacking out the syringe barrels is helpful in avoiding any detection or believed detection as to a quality of a dosage or differences between dosages, the syringes are often filled at different facilities and/or in different batches. Because rigid needle shields are not standardized, syringes filled at different facilities or in different batches may have rigid needle shields that have different appearances. For example, rigid needle shields may differ based on configuration, size, and/or color. Perceived differences in rigid needle shields by a recipient may be an indication to the recipient as to differences in the dosages. Furthermore, even if there are no differences in the dosages being delivered, such perceived differences in rigid needle shields may cause the recipient to believe that there are differences in the dosages being delivered Eliminating the ability of both the recipient and the person delivering a dosage to determine differences in the dosages or to believe that there are differences in the dosage can be vital to the efficacy and fidelity of the clinical trial.

Accordingly, what is needed in the art are syringe assemblies and parts thereof that overcome all or some of the above shortcomings.

SUMMARY OF THE INVENTION

In a first independent aspect of the present invention, a blinding cap is provided for covering a rigid needle shield that is covering a needle of a syringe, the blinding cap comprising:

an elongated body extending between a proximal end and an opposing distal end, the body at least partially bounding a chamber;
an annular sleeve projecting from the proximal end of the body and at least partially bounding a channel; and
a first flange radially inwardly projecting from the body into the chamber, the first flange at least partially bounding an opening that provides communication between the chamber and the channel.

In one embodiment, the flange is configured so that when the blinding cap covers a rigid needle shield that covers a needle, the flange is disposed proximally behind a proximal end face of the rigid needle shield for use in removing the rigid needle shield from off the needle.

In another embodiment, the chamber has a cylindrical configuration.

In another embodiment, the chamber is completely enclosed except for the opening that communicates with the chamber.

In another embodiment, the body has an exterior surface with a cylindrical configuration.

In another embodiment, the sleeve and the body share a common central longitudinal axis.

In another embodiment, the channel has a cylindrical configuration.

In another embodiment, the sleeve has an exterior surface with a cylindrical configuration.

In another embodiment, the chamber and the channel share a common central longitudinal axis.

In another embodiment, the first flange is annular and the opening centrally extends therethrough.

In another embodiment, a second flange radially inwardly projecting from the body into the chamber, the second flange being spaced apart from the first flange.

In another embodiment, the body includes:
a sidewall that extends between the proximal end and the opposing distal end and encircles the chamber;
a distal end wall disposed at the distal end of the sidewall and partially bounds the chamber; and
a proximal end wall disposed at the proximal end of the sidewall and partially bounds the chamber.

In another embodiment, the first flange radially inwardly projects from the proximal end wall or the sidewall.

In another embodiment, the sleeve projects proximally away from the proximal end wall.

In another embodiment, the chamber of the body has a diameter and the channel of the sleeve has a diameter, the diameter of the chamber being larger than the diameter of the channel.

In another embodiment, the body has an outer diameter and the sleeve has an outer diameter, the outer diameter of the body being larger than the outer diameter of the sleeve.

In another embodiment, the body and the sleeve are opaque.

In another embodiment, the blinding cap further includes:
a first cap portion comprising:
an first body portion having an interior surface and an opposing exterior surface that extend between a proximal end and an opposing distal; and
a first sleeve portion projecting from the proximal end of the first body portion and having an interior surface and an opposing exterior surface;
a second cap portion comprising:
a second body portion having an interior surface and an opposing exterior surface that extend between a proximal end and an opposing distal end; and a second sleeve portion projecting from the proximal end of the second body portion and having an interior surface and an opposing exterior surface;

means for securely coupling together the first cap portion and the second cap portion, wherein when the first cap portion is coupled with the second cap portion by the means for coupling, the first body portion and the second body portion combine to form the body and the first sleeve portion and the second sleeve portion combine to form the sleeve.

In another embodiment, the blinding cap further includes:

the first cap portion comprising a first flange portion radially inwardly projecting from the interior surface of the first body portion; and the second cap portion comprising a second flange portion radially inwardly projecting from the interior surface of the second body portion;

wherein when the first cap portion is coupled with the second cap portion by the means for coupling, the first flange portion and the second flange portion combine to form the first flange.

In another embodiment, the first cap portion and the second cap portion are separate and discrete members.

In another embodiment, the first cap portion and the second cap portion are connected together by a hinge.

In another embodiment, the first cap portion and the second cap portion are connected together by a living hinge and are formed as single integral continuous member.

In another embodiment, the means for securely coupling together the first cap portion and the second cap portion comprises a projection extending from first cap portion and a recess formed on the second cap portion, the recess being configured to receive the projection so as to secure the first cap portion to the second cap portion.

In another embodiment, the blinding cap further includes:

the projection comprising an elongated rib projecting from the first body portion of the first cap portion, a detent outwardly projecting from the rib; and the recess comprising an elongated notch formed on the second body portion of the second cap portion, the elongated notch being bounded by a face having slot formed therein, the notch being configured to receive the elongated rib so that the detent is received in the slot.

In another aspect of the present invention, a syringe assembly includes:

a syringe comprising:

a syringe barrel having a proximal end and an opposing distal end; and a needle projecting from the distal end of the syringe barrel;

a rigid needle shield having a proximal end that terminates at a proximal end face and an opposing distal end, a cavity being recessed into the through the proximal end face, the proximal end of the rigid needle shield being removably coupled to the distal end of the syringe barrel so that the needle is received within the cavity of the rigid needle shield; and the blinding cap as recited in claim 1 and disposed over at least a portion of the rigid needle shield, the first flange of the blinding cap being disposed proximally behind the proximal end face of the rigid needle shield so that as the blinding cap is moved distally relative to the syringe barrel, the first flange of the blinding cap engages against the proximal end face of the rigid needle shield.

In a second independent aspect of the present invention, a syringe assembly includes:

a syringe comprising:

a syringe barrel having a proximal end and an opposing distal end; and a needle projecting from the distal end of the syringe barrel;

a rigid needle shield having a proximal end that terminates at a proximal end face and an opposing distal end, a cavity being recessed into the rigid needle shield through the proximal end, the proximal end of the rigid needle shield being removably coupled to the distal end of the syringe barrel so that the needle is received within the cavity of the rigid needle shield; and a blinding cap disposed over at least a portion of the rigid needle shield, a portion of the blinding cap being disposed proximally behind the proximal end face of the rigid needle shield so that as the blinding cap is moved distally relative to the syringe barrel, the portion of the blinding cap engages against the proximal end face of the rigid needle shield.

In one embodiment, the cavity is recessed into the rigid needle shield through the proximal end face.

In another embodiment, the blinding cap includes:

an elongated body extending between a proximal end and an opposing distal end, the body bounding a chamber; and the portion of the blinding cap comprising a flange projecting from the body into the chamber.

In another embodiment, a slot is formed between a proximal end face of the rigid needle shield and a portion of the distal end of the syringe, the flange being received within the slot.

In another embodiment, the blinding cap completely encircles the rigid needle shield.

In another embodiment, the blinding cap is opaque.

In another embodiment, the blinding cap further includes an annular sleeve projecting from the proximal end of the body, the sleeve encircling a portion of the distal end of the syringe barrel.

In another embodiment, the sleeve has an outer diameter and the body has an outer diameter, the outer diameter of the body being larger than the outer diameter of the sleeve.

In another embodiment, the flange is annular and bounds a central opening.

In another embodiment, the blinding cap includes:

a first cap portion comprising:

a first body portion having an interior surface and an opposing exterior surface that extend between a proximal end and an opposing distal; and a first flange portion radially inwardly projecting from the interior surface of the first body portion;

a second cap portion comprising:

a second body portion having an interior surface and an opposing exterior surface that extend between a proximal end and an opposing distal; and a second flange portion radially inwardly projecting from the interior surface of the second body portion; and means for securely coupling together the first cap portion and the second cap portion, wherein when the first cap portion is coupled to the second cap portion by the means for securely coupling, the first body portion and the second body portion combine to form the body and the first flange portion and the second flange portion combine to form the flange.

In another embodiment, the first cap portion and the second cap portion are separate and discrete members.

In another embodiment, the first cap portion and the second cap portion are connected together by a hinge.

In another embodiment, the first cap portion and the second cap portion are connected together by a living hinge and are formed as single integral continuous member.

In another embodiment, the syringe assembly further includes:
- a first sleeve portion projecting from the proximal end of the first body portion; and
- a second sleeve portion projecting from the proximal end of the second body portion, the first sleeve portion and the second sleeve portion combining to form an annular sleeve that encircles a portion of the distal end of the syringe barrel.

In another embodiment, the means for securely coupling together the first cap portion and the second cap portion comprises a projection extending from first cap portion and a recess formed on the second cap portion, the recess being configured to receive the projection so as to secure the first cap portion to the second cap portion.

The second aspect of the invention may include any of the features, options and possibilities set out elsewhere in this document, including in the above first aspect and in later discussed aspects.

In a third independent aspect of the present invention, a method for assembling a syringe assembly includes:
- positioning a first cap portion adjacent to a rigid needle shield, the rigid needle shield being removably secured to a distal end of a syringe barrel and housing a needle projecting from the syringe barrel; and
- securing a second cap portion to the first cap portion to form a blinding cap that covers the rigid needle shield, a portion of the blinding cap being disposed proximally behind a proximal end face of the rigid needle shield.

In another embodiment, the blinding cap covers at least a portion of the distal end of the syringe barrel.

In another embodiment, the blinding cap includes:
- a body bounding a chamber, the rigid needle shield being disposed within the chamber; and
- the portion of the blinding cap comprising a flange radially inwardly projecting from the body into the chamber.

In another embodiment, the method further includes attaching a seal that extends between the blinding cap and the syringe barrel.

In another embodiment, the method further includes pulling the blinding cap distally relative to the syringe barrel so that the portion of the blinding cap engages against the proximal end face of the rigid needle shield and separates the rigid needle shield from the syringe barrel.

The third aspect of the invention may include any of the features, options and possibilities set out elsewhere in this document, including in the above first and second aspect and in later discussed aspects.

In a fourth independent aspect of the present invention, a method for assembling a syringe assembly includes:
- securing a blinding cap over at a rigid needle shield, the rigid needle shield being removably secured to a distal end of a syringe barrel and housing a needle projecting from the syringe barrel, a portion of the blinding cap being disposed proximally behind a proximal end face of the rigid needle shield; and
- pulling the blinding cap distally relative to the syringe barrel so that the portion of the blinding cap engages against the proximal end face of the rigid needle shield and separates the rigid needle shield from the syringe barrel.

In another embodiment, the rigid needle shield is disposed within the blinding cap as the rigid needle shield is separated from the syringe barrel.

In another embodiment, the step of securing the blinding cap comprises sandwiching the rigid needle shield between two portions of the blinding cap.

In another embodiment, the step of securing the blinding cap comprises blinding cap covering at least a portion of the distal end of the syringe barrel.

In another embodiment, the blinding cap includes:
- a body bounding a chamber, the rigid needle shield being received within the chamber; and
- the portion of the blinding cap comprising a flange radially inwardly projecting from the body into the chamber.

The fourth aspect of the invention may include any of the features, options and possibilities set out elsewhere in this document, including in the above first, second, and third aspects.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
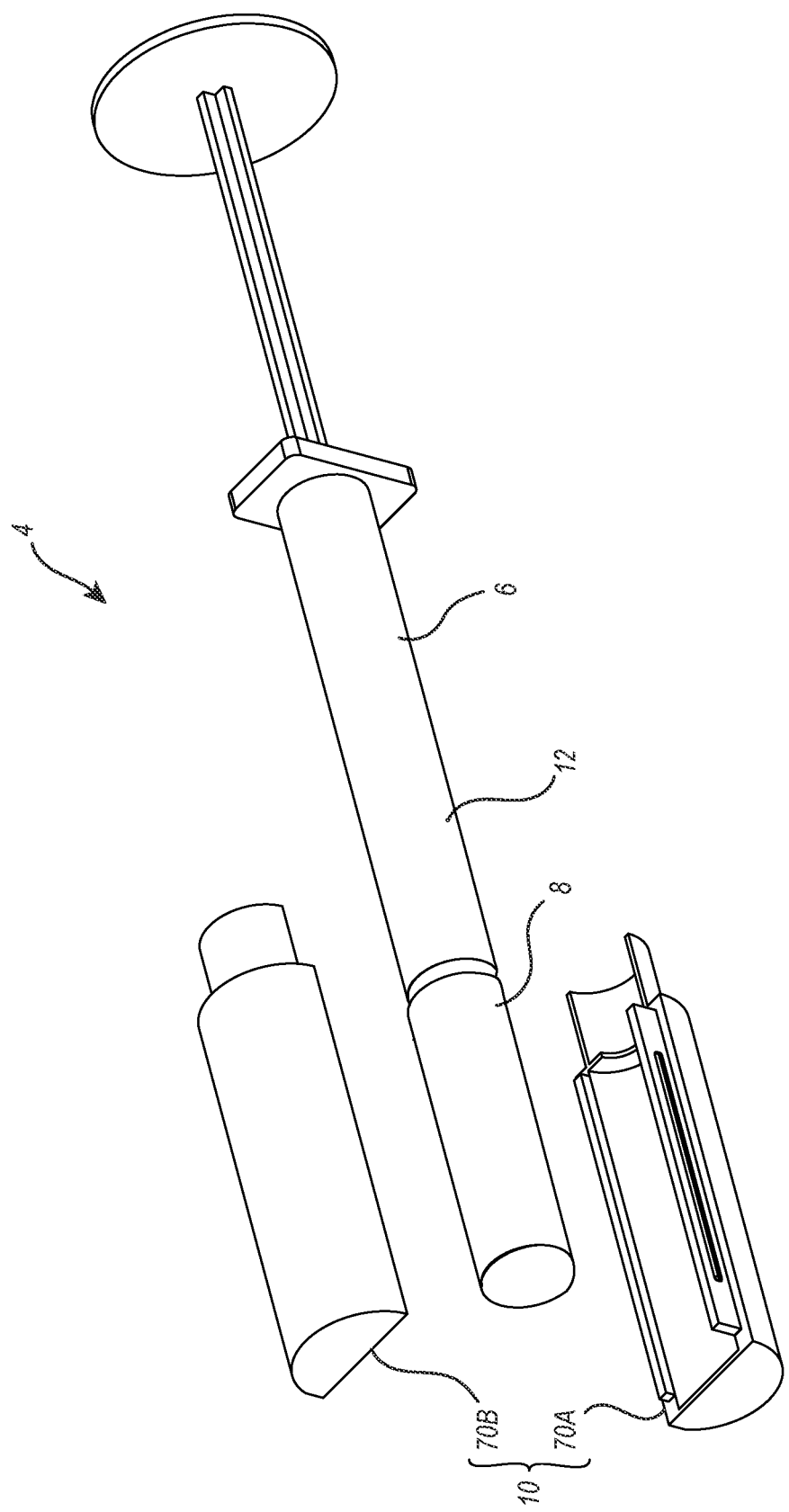
FIG. 1 is a perspective view of a syringe assembly with an exploded blinding cap.

Before describing the present disclosure in detail, it is to be understood that this disclosure is not limited to particularly exemplified apparatus, systems, methods, or process parameters that may, of course, vary. It is also to be understood that the terminology used herein is only for the purpose of describing particular embodiments of the present invention, and is not intended to limit the scope of the invention in any manner.

All publications, patents, and patent applications cited herein, whether supra or infra, are hereby incorporated by reference in their entirety to the same extent as if each individual publication, patent, or patent application was specifically and individually indicated to be incorporated by reference.

The term "comprising" which is synonymous with "including," "containing," or "characterized by," is inclusive or open-ended and does not exclude additional, unrecited elements or method steps.

It will be noted that, as used in this specification and the appended claims, the singular forms "a," "an" and "the" include plural referents unless the content clearly dictates otherwise. Thus, for example, reference to a "flange" includes one, two, or more flanges.

As used in the specification and appended claims, directional terms, such as "top," "bottom," "left," "right," "up," "down," "upper," "lower," "proximal," "distal" and the like are used herein solely to indicate relative directions and are not otherwise intended to limit the scope of the invention or claims.

Where possible, like numbering of elements have been used in various figures. Furthermore, multiple instances of an element and or sub-elements of a parent element may each include separate letters appended to the element number. For example two instances of a particular element "10" may be labeled as "10A" and "10B". In that case, the element label may be used without an appended letter (e.g., "91") to generally refer to instances of the element or any one of the elements. Element labels including an appended letter (e.g., "10A") can be used to refer to a specific instance of the element or to distinguish or draw attention to multiple uses of the element. Furthermore, an element label with an appended letter can be used to designate an alternative design, structure, function, implementation, and/or embodiment of an element or feature without an appended letter. Likewise, an element label with an appended letter can be used to indicate a sub-element of a parent element. For instance, an element "12" can comprise sub-elements "12A" and "12B."

Various aspects of the present devices and systems may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present. Furthermore, as used herein, the terms "connection," "connected," and the like do not necessarily imply direct contact between the two or more elements.

Various aspects of the present devices, systems, and methods may be illustrated with reference to one or more examplary embodiments. As used herein, the term "embodiment" means "serving as an example, instance, or illustration," and should not necessarily be construed as preferred or advantageous over other embodiments disclosed herein.

Unless defined otherwise, all technical and scientific terms used herein have the same meaning as commonly understood by one of ordinary skill in the art to which the present disclosure pertains. Although a number of methods and materials similar or equivalent to those described herein can be used in the practice of the present disclosure, the preferred materials and methods are described herein.

In general, the present invention is directed to syringe assemblies and blinding caps that form part of the syringe assemblies. The blinding cap coves a rigid needle shield coupled to a syringe as part of a blinded testing protocol. Specifically, the blinding cap covers the rigid needle shield and, in some embodiments, a distal end of a syringe barrel so as to prevent a patient and a person delivering a dosage from discerning differences between rigid needle shields. Discerning differences in rigid needle shields could cause the patient to determine differences in dosages being administered or to be believe that there are differences in the dosages being administered, thereby influencing the results of the blinded study. The blinding cap also assists in removal of the rigid needle shield from the syringe.

Depicted in FIG. 1 is one embodiment of a syringe assembly 4 incorporating features of the present invention. In general, syringe assembly 4 comprises a syringe 6 used for dispensing a liquid dosage, a rigid needle shield 8 removably coupled with syringe 6, and a blinding cap 10 that can be used to selectively cover needle shield 8. More specifically, with reference to FIG. 2, syringe 6 comprises syringe barrel 12 that includes an elongated cylindrical body 20 having an interior surface 22 and an exterior surface 24 that longitudinally extend between a proximal end 26 and an opposing distal end 28. Interior surface 22 bounds a compartment 30 that extends between opposing ends 26 and 28. Compartment 30 holds a liquid dosage. The liquid dosage can comprise a drug dosage, a corresponding placebo dosage, or a comparator dosage. An opening 31 is formed at proximal end 26 and communicates with compartment 30. A flange 32 radially outwardly projects from proximal end 26. Flange 32 can encircle proximal end 26 or can project out from opposing sides of proximal end 26.

Projecting from body 20 at distal end 28 is an elongated stem 34. Stem 34 has a transverse cross section with a diameter that is smaller than a diameter of the transverse cross section of body 20. As discussed below, stem 34 is configured to receive and engage needle shield 8. Syringe barrel 12, or at least body 20, is typically made of a transparent or semi-transparent material such as clear plastic or glass. In this embodiment, however, syringe barrel 12 is blacked out, i.e., made opaque, so that the liquid dosage cannot be seen through syringe barrel 12. This can be accomplished by applying a layer, coating, or structure over syringe barrel 12. For example, syringe barrel 12 could be painted or a printing could be applied. In other embodiments, an adhesive layer, wrap, or some other structure could be placed over syringe barrel 12. Other approaches can also be used so that syringe barrel 12 is blacked out. In other embodiments, syringe barrel 12 can be made of an opaque material.

Projecting from stem 34 of syringe barrel 12 along a central longitudinal axis 37 of body 20 is a tubular needle 36. Needle 36 has a proximal end 33 that communicates with compartment 30 of syringe barrel 12 and an opposing distal end 35 that terminates at a sharpened tip 38. Needle 36 is typically made of metal. In the embodiment depicted, needle 36 is permanently attached to syringe barrel 12, such as by being molded into stem 34 or by being attached by an adhesive. In alternative embodiments, needle 36 can be removably and/or mechanically attached to stem 34 or the combination of needle 36 and stem 34 can be removably and/or mechanically attached to body 20. For example, stem 34 and needle 36 can be formed with complementary halves of a luer-lock or snap-fit connection that permits fluid coupling therebetween. Other types of fluid connections can also be used.

Needle shield 8 has a proximal end 40 that terminates at a proximal end face 41 and an opposing distal end 42 that terminates at a distal end face 48. Needle shield 8 has an interior surface 43 that bounds a cavity 44. An opening 45 is formed on proximal end face 41 that communicates with cavity 44. Expressed in other terms, cavity 44 is recessed into needle shield 8 through proximal end face 41. Cavity 44 is configured to receive needle 36 and at least a portion of stem 34 so that a releasable friction tight engagement is formed between interior surface 43 and stem 34.

When needle shield 8 is attached to syringe barrel 12 by the friction tight engagement, needle 36 is safely enclosed within cavity 44. Needle shield 8 typically has a portion comprised of a rigid plastic that prevents needle 36 from puncturing therethrough and a more flexible or elastomeric portion that engages with stem 34. Needle shield 8 is selectively removed from syringe barrel 12 by simply pulling needle shield 8 distally relative to syringe barrel 12. In alternative embodiments, a mechanical connection can be used to secure needle shield 8 to syringe barrel 12. For example, needle shield 8 and stem 34 can be formed with complementary halves of a luer-lock connection that permit coupling therebetween. In this embodiment, needle shield 8 is removed by first rotating needle shield 8 relative to syringe barrel 12 and then pulling needle shield 8 distally relative to syringe barrel 12. Other types of connection can also be used.

Slidably disposed within compartment 30 of syringe barrel 12 is a stopper 14. Stopper 14 has an annular side face 50. Encircling and radially outwardly projecting from side face 50 are one or more lip seals 56. Lip seals 56 maintain a liquid tight seal against interior surface 22 of syringe barrel 12 as stopper 14 longitudinally moves within compartment 30. Accordingly, as stopper 14 advances towards distal end 28 of syringe barrel 12, the liquid dosage within compartment 30 is dispensed out through needle 36. Stopper 14 is typically comprised of an elastomeric material that enables a slidable, sealed engagement between stopper 14 and syringe barrel 12. Other materials that will achieve the desired functional operation can also be used.

A plunger rod 16 comprises an elongated shaft 62 that extends between a proximal end 64 and an opposing distal end 66. Disposed at proximal end 64 of shaft 62 is a thumb rest 68. Distal end 66 is coupled with stopper 14. Plunger rod 16 is typically molded from a polymeric material, but other materials can also be used. By manually pressing on thumb rest 68, plunger rod 16 and stopper 14 are advanced distally within syringe barrel 12 which in turn causes the liquid dosage within compartment 30 to dispense out through needle 36.

Figure 3:
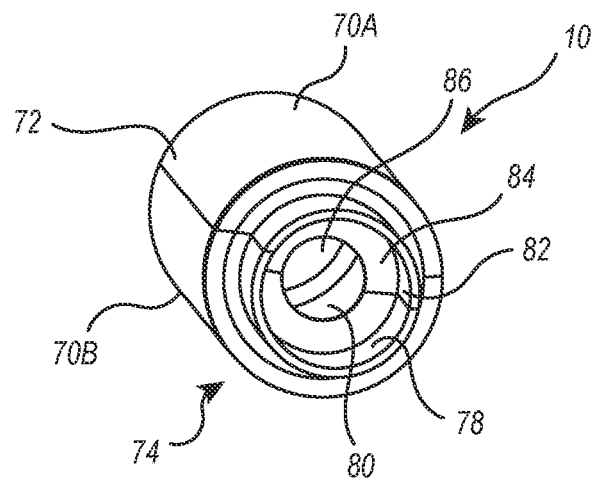
FIG. 3 is a proximal perspective view of the blinding cap shown in FIG. 1 in an assembled state.
Figure 4:
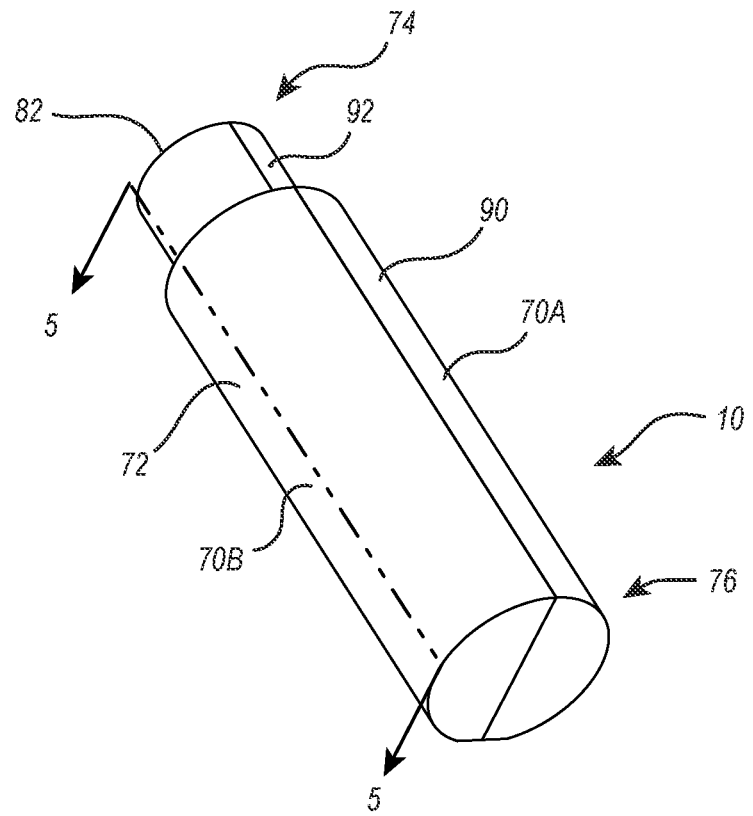
FIG. 4 is a distal perspective view of the blinding cap shown in FIG. 3.

As previously mentioned, blinding cap 10 can be used for both covering needle shield 8 and assisting in the removal of needle shield 8 from syringe 6. Blinding cap 10 can also be used for covering at least a portion of distal end 28 of syringe barrel 12. Blinding cap is shown in FIG. 1 in a disassembled state and comprises a first cap portion 70A and a second cap portion 70B that can selectively couple together around needle shield 8. Blinding cap 10 is independently shown in FIGS. 3 and 4 in an assembled state. With reference to blinding cap 10 in the assembled state, blinding cap 10 can be described as comprising a housing 72 that extends between a proximal end 74 and opposing distal end 76. Housing 72 has an interior surface 78 that bounds a compartment 80. An opening 82 is formed at proximal end 74 that communicates with compartment 80. A flange 84 radially inwardly projects from interior surface 78 into compartment 80. Flange 80 bounds a central opening 86. In the depicted embodiment, flange 84 is annular. In an alternative embodiment, however, flange 84 can comprise a plurality of separate, spaced apart flange portions.

Figure 5:
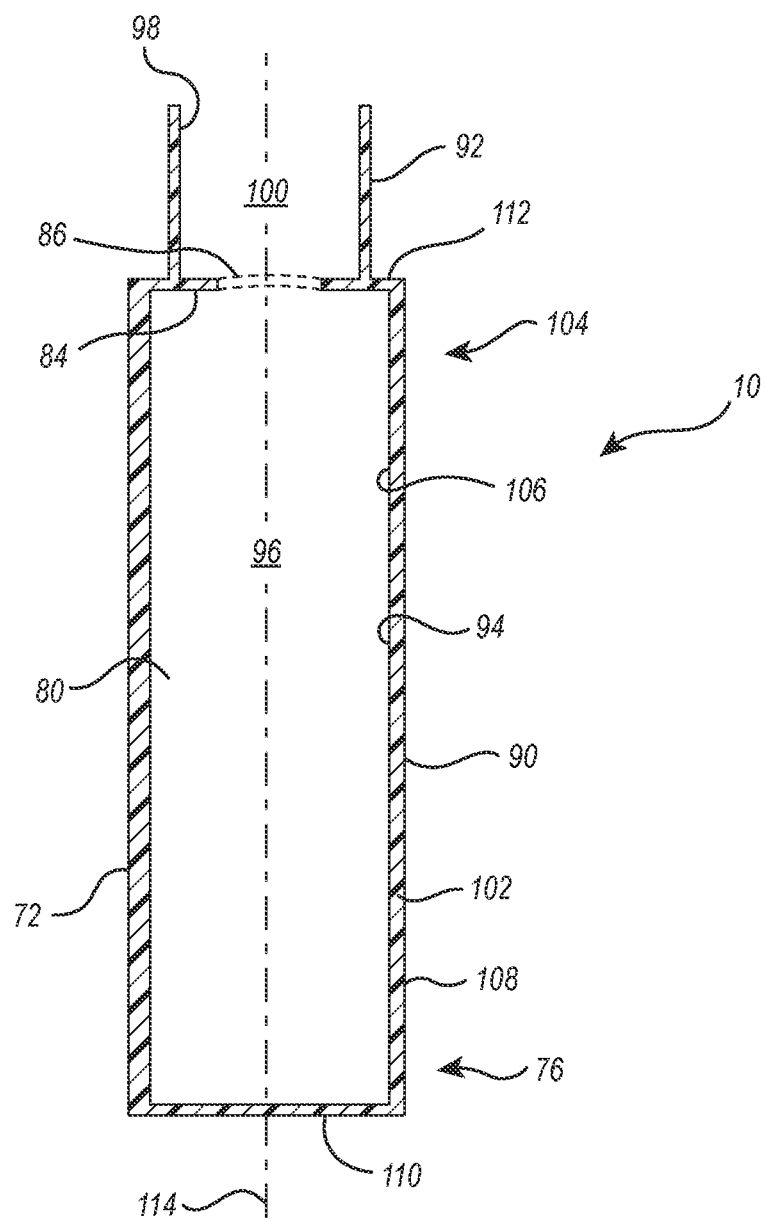
FIG. 5 is a cross sectional side view of the assembled rigid needle shield shown in FIG. 4 taken along line 5-5.

FIG. 5 is a cross sectional side view of the assembled blinding cap 10. With reference to FIG. 5, housing 72 more specifically comprises an elongated body 90 and an annular sleeve 92 projecting from body 90. In general, body 90 has an interior surface 94 that bounds a chamber 96. Sleeve 92 has in interior surface 98 that bounds a channel 100 extending therethrough. Chamber 96 and channel 100 combine to form compartment 80.

Body 90 is further described as having a sidewall 102 that extends between a proximal end 104 and distal end 76. Sidewall 102 is annular and has an interior surface 106 that encircles chamber 96 and an opposing exterior surface 108. Disposed at distal end 76 of sidewall 102 is a distal end wall 110. A proximal end wall 112 is formed at proximal end 104 of sidewall 102. Chamber 96 is at least partially bounded by sidewall 102, distal end wall 110, and proximal end wall 112. In the depicted embodiment, chamber 96 has a cylindrical configuration that is sized to receive needle shield 8. However, other configurations that will receive needle shield 8 can also be used. Body 90 and sidewall 102 are also depicted as having a cylindrical configuration. Again, other configurations can also be used.

Figure 2:
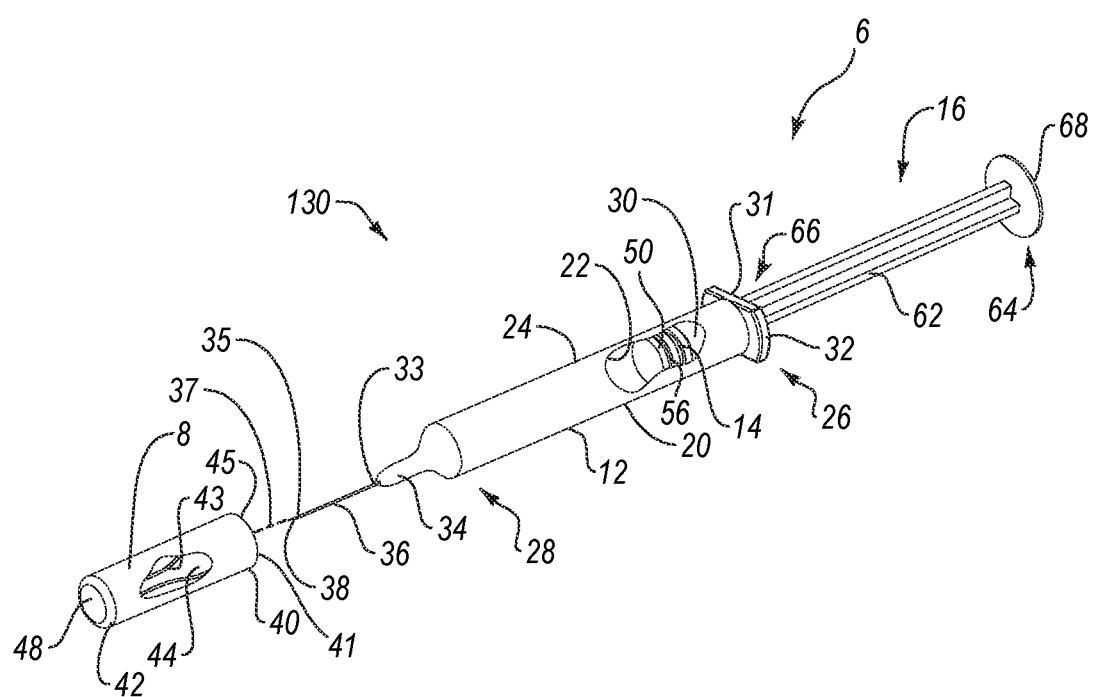
FIG. 2 is a perspective view of the syringe and rigid needle shield of the syringe assembly shown in FIG. 1.

Sleeve 92 outwardly projects from proximal end wall 112. More specifically, sleeve 92 is typically centered on proximal end wall 112 so that chamber 96 and channel 100 share a common central longitudinal axis 114. Channel 100 is configured to receive at least a portion of distal end 28 of syringe barrel 12/body 20 (FIG. 2). Sleeve 92 is depicted as annular and having a cylindrical configuration. Channel 100 is also depicted having a cylindrical configuration. In other embodiments, sleeve 92 and/or channel 100 can have other configurations.

In one embodiment of the present invention, a flange radially inwardly projects from body 90 into chamber 96 at proximal end 104. In the depicted embodiment, annular flange 84 (FIG. 3) radially inwardly projects from proximal end wall 112 into chamber 96. Annular flange 84 bounds opening 86 that provides communication between channel 100 and chamber 96. As discussed below in more detail, flange 84 can have other configurations and can be positioned at other locations.

Figure 6:
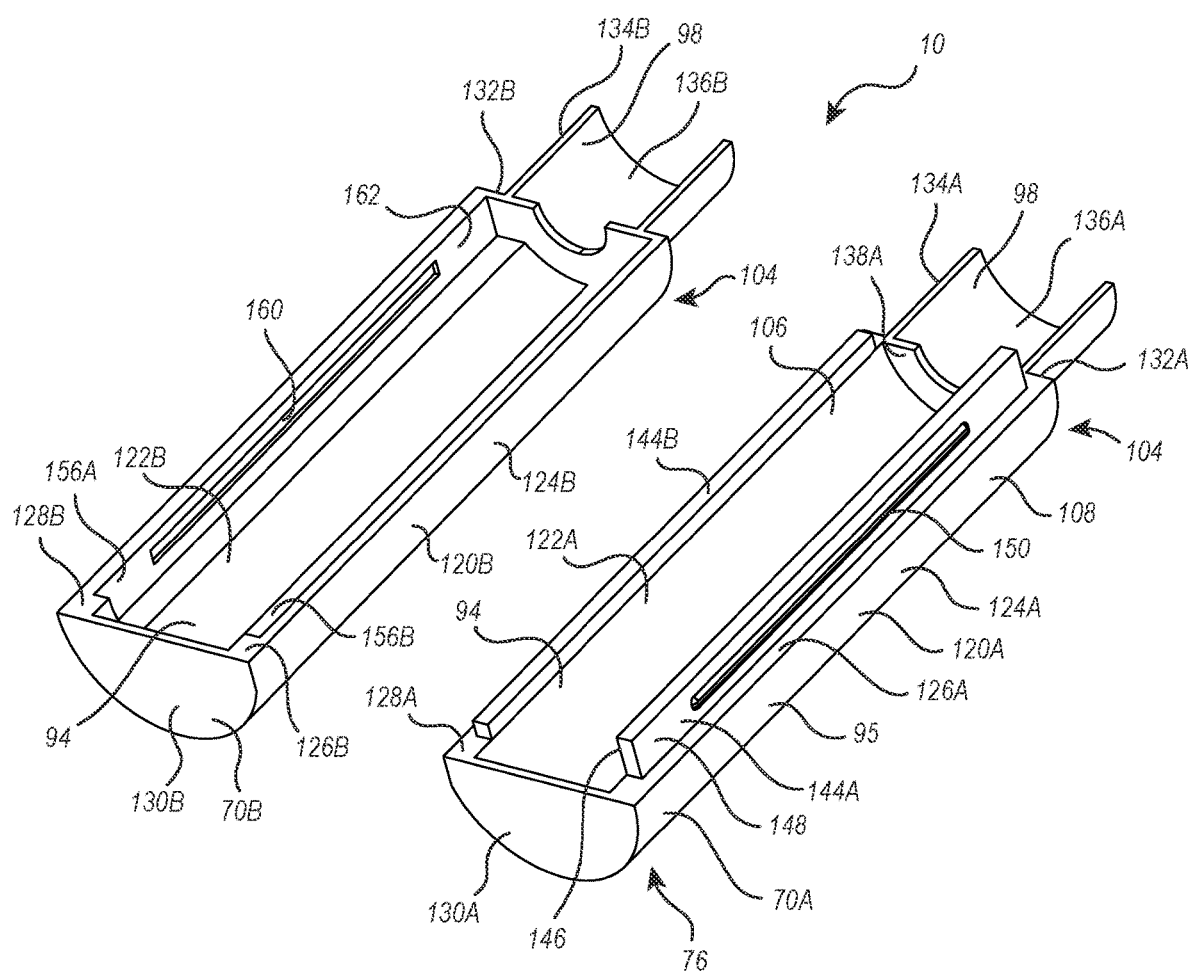
FIG. 6 is a perspective view of the cap portions of the rigid needle shield shown in FIG. 1.

Turing to FIG. 6, first cap portion 70A and second cap portion 70B of blinding cap 10 will now be discussed in detail. Specifically, first cap portion 70A comprises a first body portion 120A having a semi-cylindrical configuration with interior surface 94 and exterior surface 95 extending between proximal end 104 and distal end 76. Interior surface 94 bounds a first chamber portion 122A. First chamber portion 122A is shown having a semi-cylindrical configuration but other configurations can also be used.

Described in further detail, first body portion 120A comprises a first sidewall portion 124A having interior surface 106 and exterior surface 108 that extend longitudinally between proximal end 104 and distal end 76. First sidewall portion 124A has a semi-cylindrical configuration that extends laterally between a first edge 126A and an opposing first edge 128A. Edges 126A and 128A also extend longitudinally between proximal end 104 and distal end 76. First body portion 120A further includes a first distal end wall portion 130A at distal end 76 and a first proximal end wall portion 132A at proximal end 104. Projecting proximally from first proximal end wall portion 132A is a first sleeve portion 134A having interior surface 98 that bounds a first channel portion 136A. First sleeve portion 134A and first channel portion 136A are each depicted has having a semi-cylindrical configuration. Again, other configurations can also be used. A first flange portion 138A radially inwardly projects from first proximal end wall portion 132A into first chamber portion 122A.

Except as discussed below, in the depicted embodiment second cap portion 70B has the same configuration and structural elements at first cap portion 70A. As such, the above prior discussion of parts, configuration, elements and alternatives of first cap portion 70A are applicable to second cap portion 70B. Like elements between first cap portion 70A and second cap portion 70B are identified by like reference characters except that all corresponding reference characters on second cap portion 70B includes the suffix "B" as opposed to "A". Furthermore, the prefix "first" used in association with the named parts of first cap portion 70A is changed to "second" in association with the corresponding named parts of second cap portion 70B. For example, second cap portion 70B includes a second body portion 120B that bounds a second chamber portion 122B. Second body portion 120B comprises a second sidewall portion 124B having a semi-cylindrical configuration that extends laterally between a second edge 126B and an opposing second edge 128B. Second body portion 120B further includes a second distal end wall portion 130B at distal end 76 and a second proximal end wall portion 132B at proximal end 104. Projecting proximally from second proximal end wall portion 132B is a second sleeve portion 134B that bounds a second channel portion 136B. A second flange portion 138B radially inwardly projects from first proximal end wall portion 132B into second chamber portion 122B.

In one embodiment of the present invention, means are provided for securely coupling together first cap portion 70A and second cap portion 70B to form the assembled blinding cap 10. By way of example and not by limitation, an elongated rib 144A outwardly projects from and along the length of first edge 126A of first sidewall portion 124A of first cap portion 70A. Rib 144A has an inside face 146 facing towards first chamber portion 122A and an opposing outside face 148.

A detent 150 outwardly projects from outside face 148. In this embodiment, detent 150 is elongated and extends along the length of outside face 148. A rib 144B also outwardly projects from and extends along the length of first edge 128A of sidewall portion 124A. Rib 144B can be the same size and configuration as rib 144A and can include detent 150 on an outside face thereof. In the current embodiment, however, rib 144B is shorter in height than rib 144A and does not include detent 150.

In contrast to outwardly projecting ribs 144 on first cap portion 70A, corresponding elongated notches are formed on the second cap portion 70B and are configured to receive ribs 144A and 144B. Specifically, a first notch 156A is recessed into second edge 128B along interior surface 94. First notch 156A is elongated and is complimentary to and configured to receive first rib 144A. First notch 156A is bounded by an inside face 162 having an elongated slot 160 formed thereon that is configured to receive detent 150.

A second notch 156B is formed into edge 126B along interior surface 94. Notch 156B is likewise elongated and is complimentary to and configured to receive second rib 144B. During assembly cap portions 70A and 70B are securely together by advancing ribs 144A and 144B into notches 156A and 156B, respectively, so as to form blinding cap 10. As a result of detent 150 fitting into slot 160, cap portions 70A and 70B are securely snap-fit together, thereby preventing any unintentional separation.

It is appreciated that ribs 144 and notches 156 are only one example of means for securely coupling together first cap portion 70A and second cap portion 70B and that a variety of other securing mechanism can also be used. By way of example and not by limitation, in one alternative embodiment, one of the ribs 144 from cap portion 70A and one of the notches 156 from cap portion 70B could be switched so that each cap portion 70 has one notch and one rib. In another alternative, detent 150 and slot 160 can have a variety of different configurations. For example, one or more detents having a circular, polygonal or other configuration can be received within a recess having a complementary configuration for producing a snap-fit configuration. Furthermore, it is appreciated ribs 144 and notches 156 are only one example of projections and complementary recesses that can be used for coupling together cap portions 70A and 70B. In other embodiments, other configurations of projections and recesses can be used. For example, complementary barbs and sockets or complementary pegs and sockets can be used. Furthermore, one or more pawls could be formed on one of cap portions 70 while one or more teeth could be formed on a corresponding location of the other cap portion so as to form a ratchet that couples cap portions 70A and 70B together.

In another alternative, an adhesive can be used to secure cap portions 70A and 70B together. In yet another alternative embodiment, one or more fasteners such as a screw, spike, pin, or staple could be advanced through a portion of cap portions 70A and 70B to secure them together. In one embodiment, cap portions 70A and 70B could be configured to be mechanically press fit together. In still another embodiment, a fastener could be place around a portion of the assembled cap portions 70A and 70B to securely hold them together. For example, a clamp, crimp, tape, shrink wrap, pull tie, or the like could be secured around assembled cap portions 70A and 70B. Other mechanisms can also be used for securely coupling together first cap portion 70A and second cap portion 70B to form the assembled blinding cap 10.

Blinding cap 10 is typically molded from a plastic material although other materials can also be used. Blinding cap 10 is opaque so that needle shield 8 cannot be seen through blinding cap 10. In one embodiment, the material used to make blinding cap 10 can be opaque. In another embodiment, the material used to make blinding cap 10 to be translucent or semi-translucent but a covering, coating, tape, etching, printing, painting or other material, structure or process can be used is make blinding cap 10 opaque.

Figure 7:
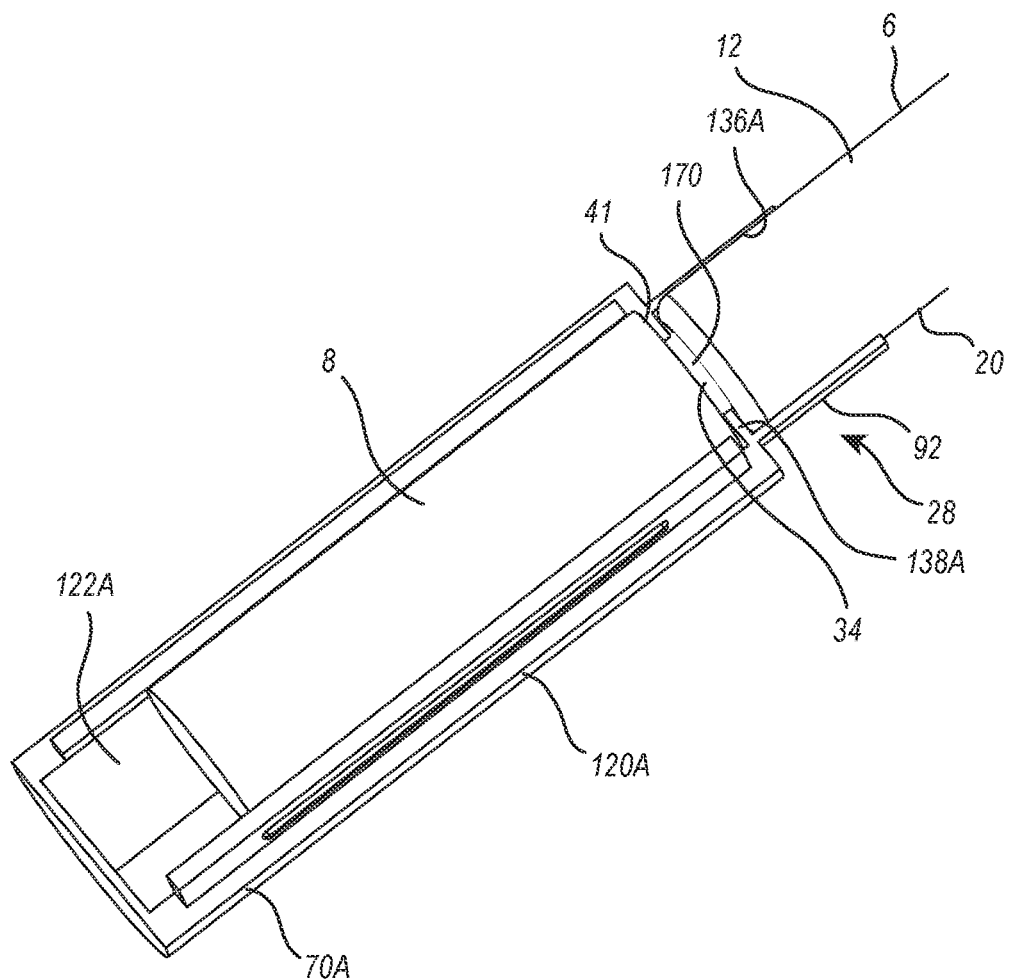
FIG. 7 is a perspective view of one of the cap portions shown in FIG. 6 disposed on the rigid needle shield and the distal end of the syringe shown in FIG. 1.

Turning to FIG. 7, an annular slot 170 is formed between proximal end face 41 of needle shield 8 and a portion of syringe barrel 12 at distal end 28. For example, slot 170 can be formed between proximal end face 41 and a distal terminus of body 20 or a portion of stem 34. During assembly, one of cap portions 70A or 70B (depicted and discussed as 70A in FIG. 7) is positioned so that needle shield 8 is received within first chamber portion 122A, a portion of distal end 28 of syringe barrel 12 is received within first channel portion 136A, and first flange portion 138A is received within slot 170. A portion of stem 34 of syringe barrel 12 passes through opening 86 (FIG. 5) bounded by flange portion 138A. In this position, flange portion 138A is disposed proximally of proximal end face 41 of needle shield 8 and disposed against or adjacent to proximal end face 41 so that if cap portion 70A was moved distally relative to syringe barrel 12, flange portion 138A would push against proximal end face 41.

Figure 8:
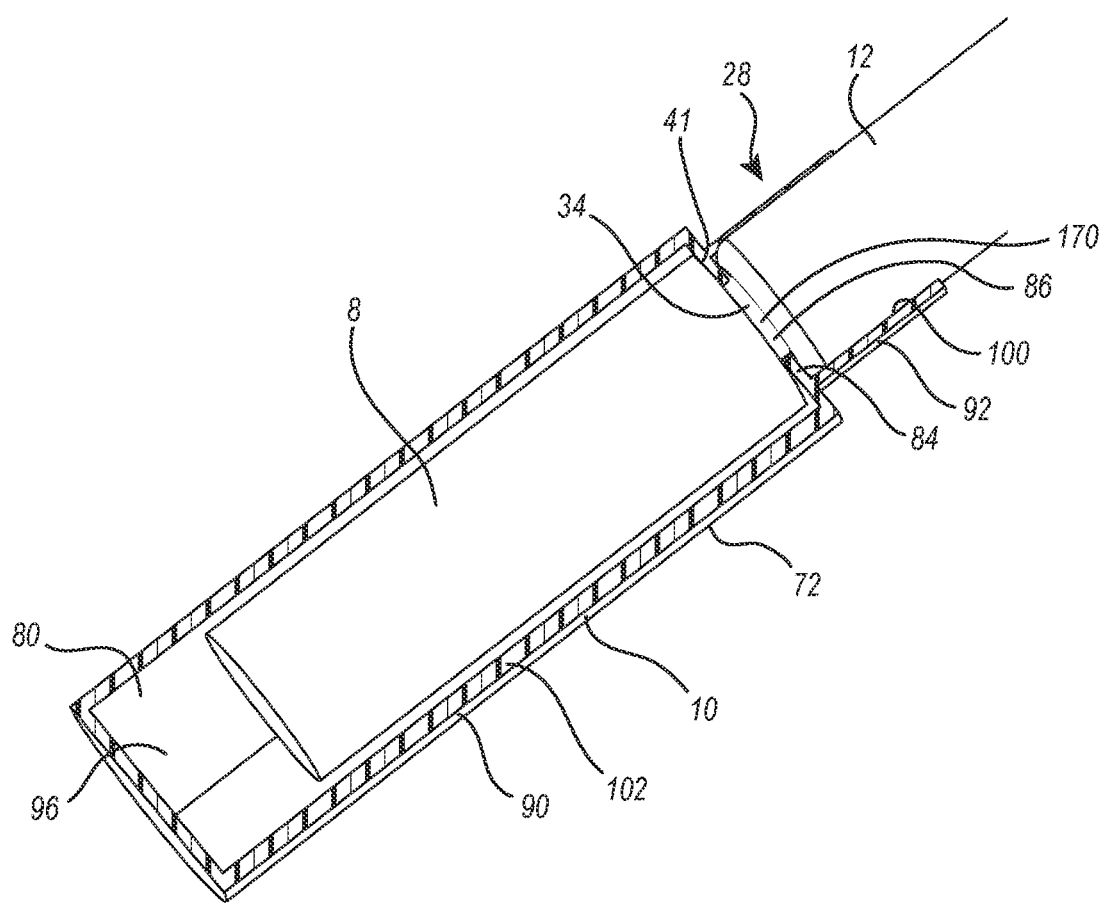
FIG. 8 is a cross sectional side view of the assembled blinding cap shown in Figure enclosing the rigid needle shield and the distal end of the syringe shown in FIG. 1.

Next, cap portion 70B is coupled with cap portion 70A, as discussed above, so that needle shield 8 and distal end 28 of syringe barrel 12 are captured and enclosed between cap portions 70A and 70B which now form blinding cap 10. More specifically, with reference to FIG. 8, which is a cross sectional side view of the assembled blinding cap 10 disposed on syringe 6, needle shield 8 is now captured and enclosed within compartment 80 of housing 72 or, more specifically, within chamber 96 of body 90. Distal end 28 of syringe barrel 12 is also captured and enclosed within compartment 80 of housing 72 or, more specifically, within channel 100 of sleeve 92. Flange 84 is received within slot 170 while a portion of stem 34 of syringe barrel 12 passes through opening 86 bounded by flange 84. In this position, flange 84 is disposed proximally of proximal end face 41 of needle shield 8 and is disposed against or adjacent to proximal end face 41 so that when blinding cap 10 is moved distally relative to syringe barrel 12, flange 84 pushes against proximal end face 41 of needle shield 8.

In this assembled configured, needle shield 8 is completely covered by the combination of blinding cap 10 and syringe barrel 12 so that neither a patient nor others handling syringe assembly 4 can discern differences based on needle shield 8. Sleeve 92 can serve a couple of different functions. For example, sleeve 92 helps to cover/hide proximal end face 41 of needle shield 8. However, sleeve 92 also helps to cover/hide distal end 28 of syringe barrel 12 and, more specifically, stem 34 and the distal end of body 20. Different syringes may have different configurations and different couplings between syringe barrel 12 and needle 36 (FIG. 2). Sleeve 92 helps to cover/hide all of these potentially discerning features. Sleeve 92 will typically have a length that is at least or less than 3 mm, 5 mm, 7 mm, 10 mm, 15 mm, or 20 mm or is in a range between any two of the forgoing. Sleeve 92 will also typically sit flush against the side of syringe barrel 12 or be spaced apart from the side of syringe barrel 12 by a distance that is at least or less than 0.5 mm, 1 mm, 2 mm or 4 mm.

It is noted that needle shield 8 can be freely disposed within chamber 96 of blinding cap 10 so that rotation of blinding cap 10 relative to syringe barrel 12 does not facilitate rotation of needle shield 8 or at least does not facilitate complete concurrent rotation needle shield 8. For example, the inner diameter of chamber 96 can be larger than the outer diameter needle shield 8 so that needle shield 8 does not directly contact sidewall 102 of body 90. More specifically, needle shield 8 and sidewall 102 of body 90 can be spaced apart by an open space having a distance that is at least or less then 1 mm, 2 mm, 3 mm or 5 mm or is in a range between any two of the foregoing. One of the benefits of having chamber 96 larger than needle shield 8 is that blinding cap 10 can be easily secured over a variety of different sizes and shapes of needle shields without risk of interference by the needle shields. Alternatively, needle shield 8 can bias or sit directly against sidewall 102 of body 90. Needle shield 8 can also be securely held within chamber 96 of blinding cap 10 so that rotation of blinding cap 10 relative to syringe barrel 12 causes concurrent rotation of needle shield 8. This can be caused by direct frictional engagement between needle shield 8 and sidewall 102 of body 90. Alternatively, to help facilitate engagement between blinding cap 10 and needle shield 8, a flexible material, adhesive or the like can be positioned within chamber 96 of blinding cap 10 that will ensure a secure frictional engagement or adhesive engagement between sidewall 102 of blinding cap 10 and needle shield 8 when needle shield 8 is disposed within chamber 96.

Figure 9:
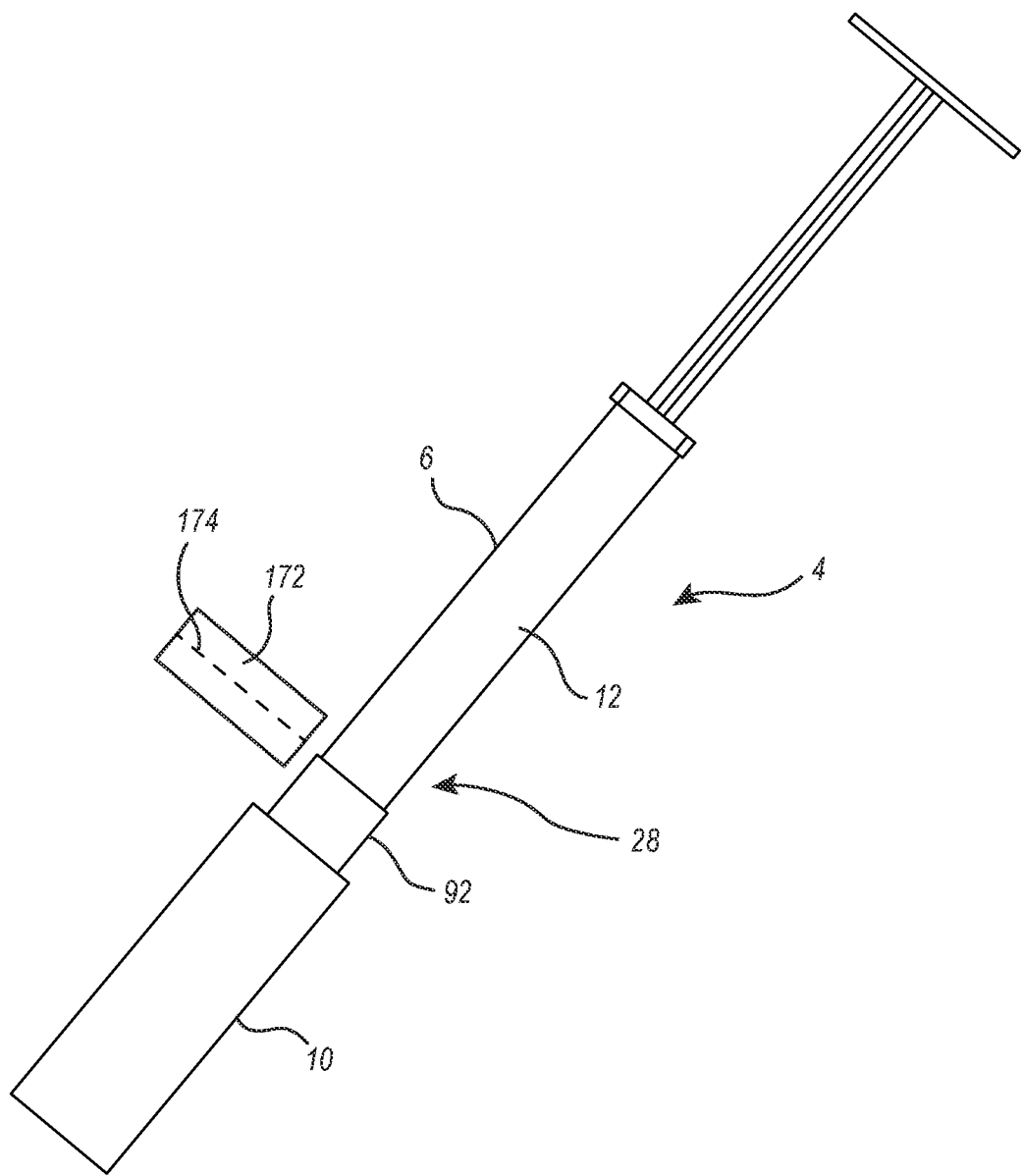
FIG. 9 is an elevated side view of the fully assembled syringe assembly shown in FIG. 8 with an optional seal ready for attachment.
Figure 10:
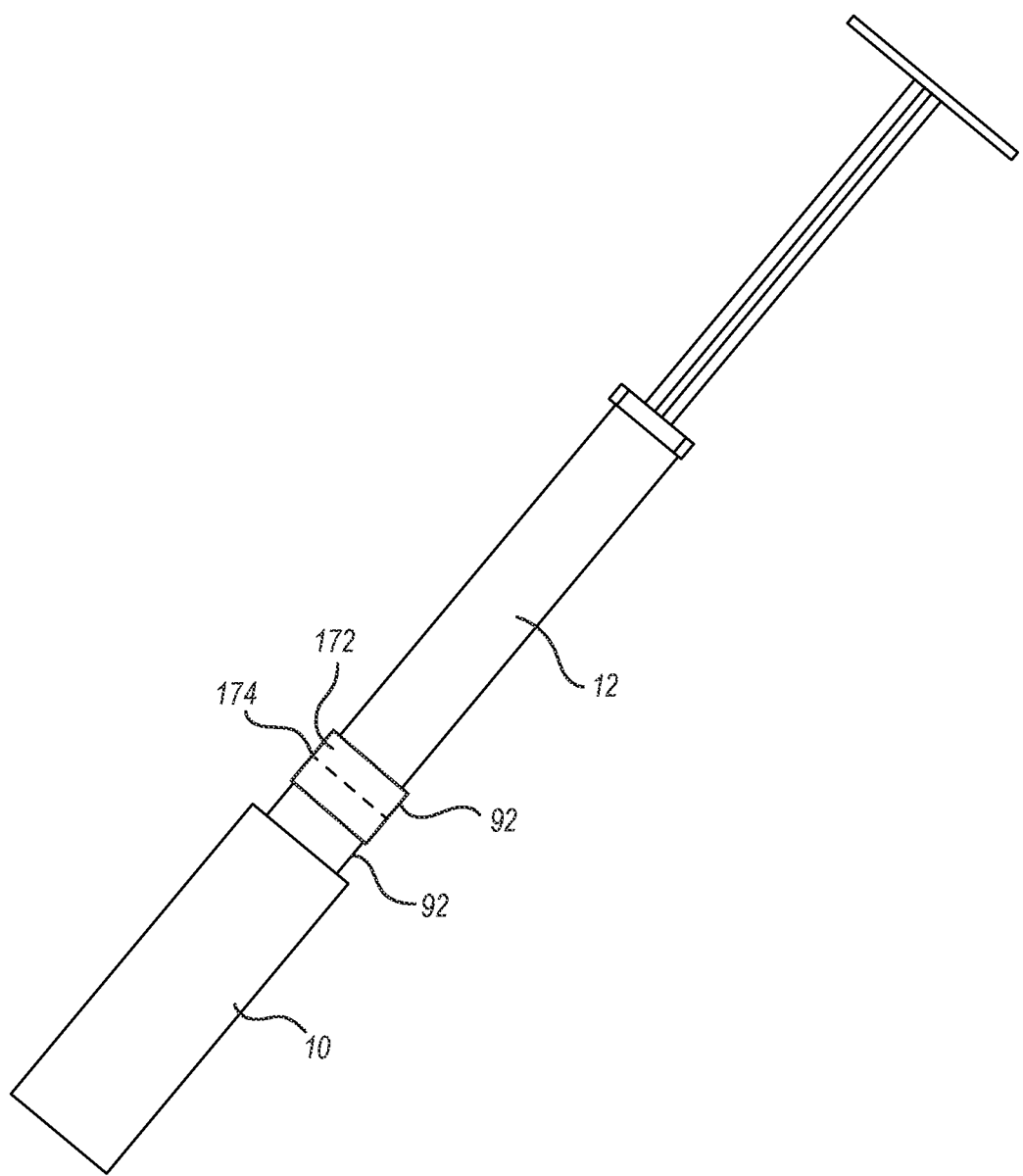
FIG. 10 is an elevated side view of the syringe assembly shown in FIG. 9 with the optional seal attached thereto.

With reference to FIG. 9, to help ensure no tampering with syringe assembly 4 or any undesired removal of needle shield 8 or blinding cap 10, a seal 172 can be placed extending between blinding cap 10 and syringe barrel 12 and, more specifically, between sleeve 92 and distal end 28 of syringe barrel 12. In one embodiment, seal 172 can comprise a piece of tape having an adhesive on one side and having a line of spaced apart perforations, i.e., perforation line 174, that centrally extends along the length thereof. Seal 172 is wrapped around syringe assembly 4 so as to adhere to syringe assembly 4. Specifically, half of the length of seal 172 on one side of perforation line 174 is secured to sleeve 92 while the opposing half of the length of seal 172 on the other side of perforation line 174 is secured to syringe barrel 12, as depicted in FIG. 10. Other configurations of seals can also be used.

Figure 11:
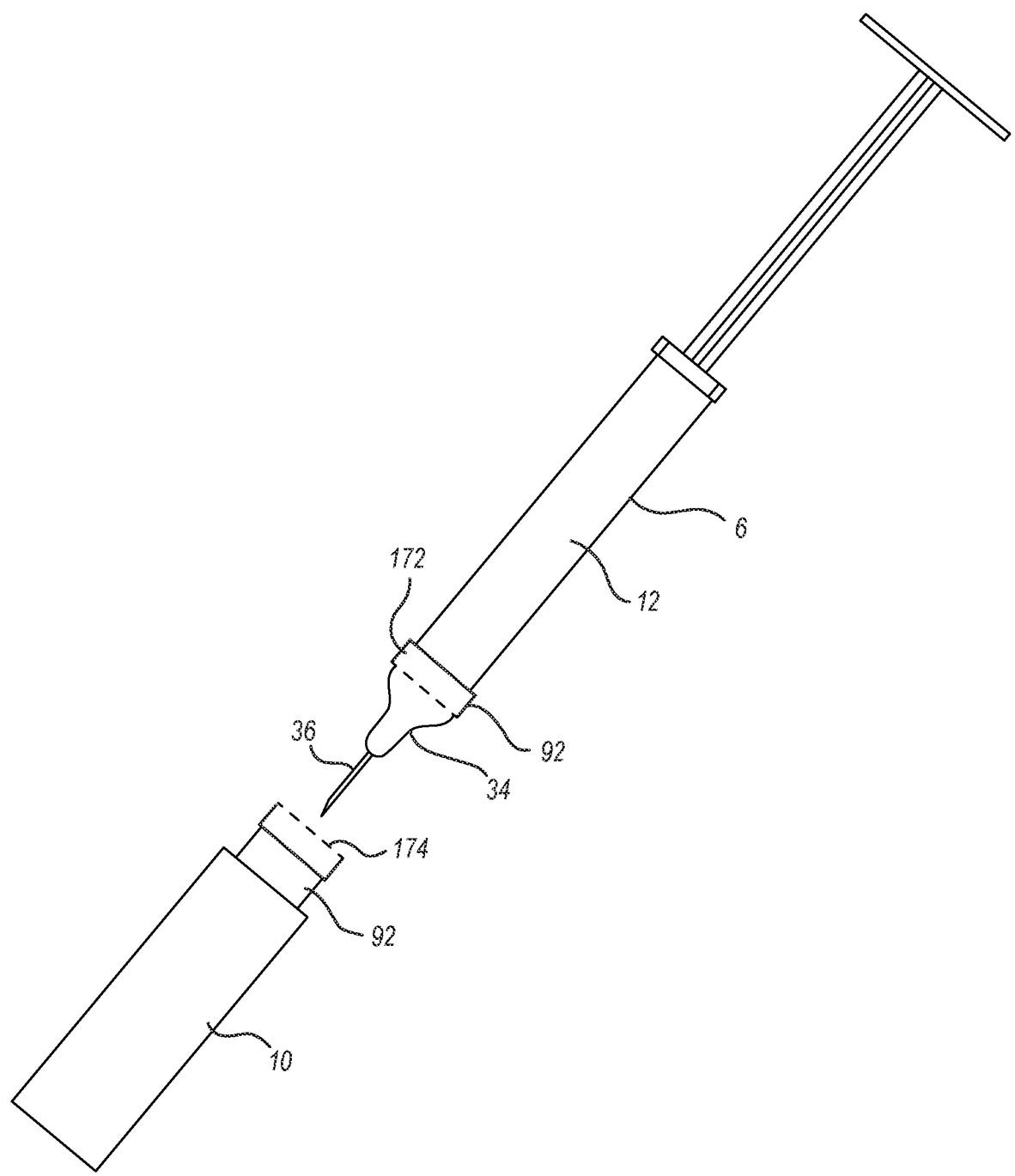
FIG. 11 is a perspective view of the blinding cap housing the rigid needle shield being separated from the syringe shown in FIG. 10 and the optional seal being broken.

To administer the dosage within syringe 6, seal 172 is first broken by manually rotating syringe barrel 12 and blinding cap 10 in opposite directions or rotating one while the other is held stationary. This rotation causes seal 172 to tear along perforation line 174. Next, once seal 172 is broken, blinding cap 10 is pulled distally relative to syringe 6/syringe barrel 12. In so doing, flange 84 (FIG. 8) pushes against proximal end face 41 of needle shield 8, thereby causing needle shield 8 and blinding cap 10 to concurrently pull off of syringe barrel 12 and needle 36 as depicted in FIG. 11. Here it is noted that flange 84 (FIG. 8) not only assists in helping to concurrently remove needle shield 8 with blinding cap 10 but, once needle shield 8 and blinding cap 10 have been removed as depicted in FIG. 11, flange 84 continues to assist in covering and obscuring needle shield 8 within blinding cap 10, thereby further limiting the ability to detect any discernable features of needle shield 8.

Figure 11A:
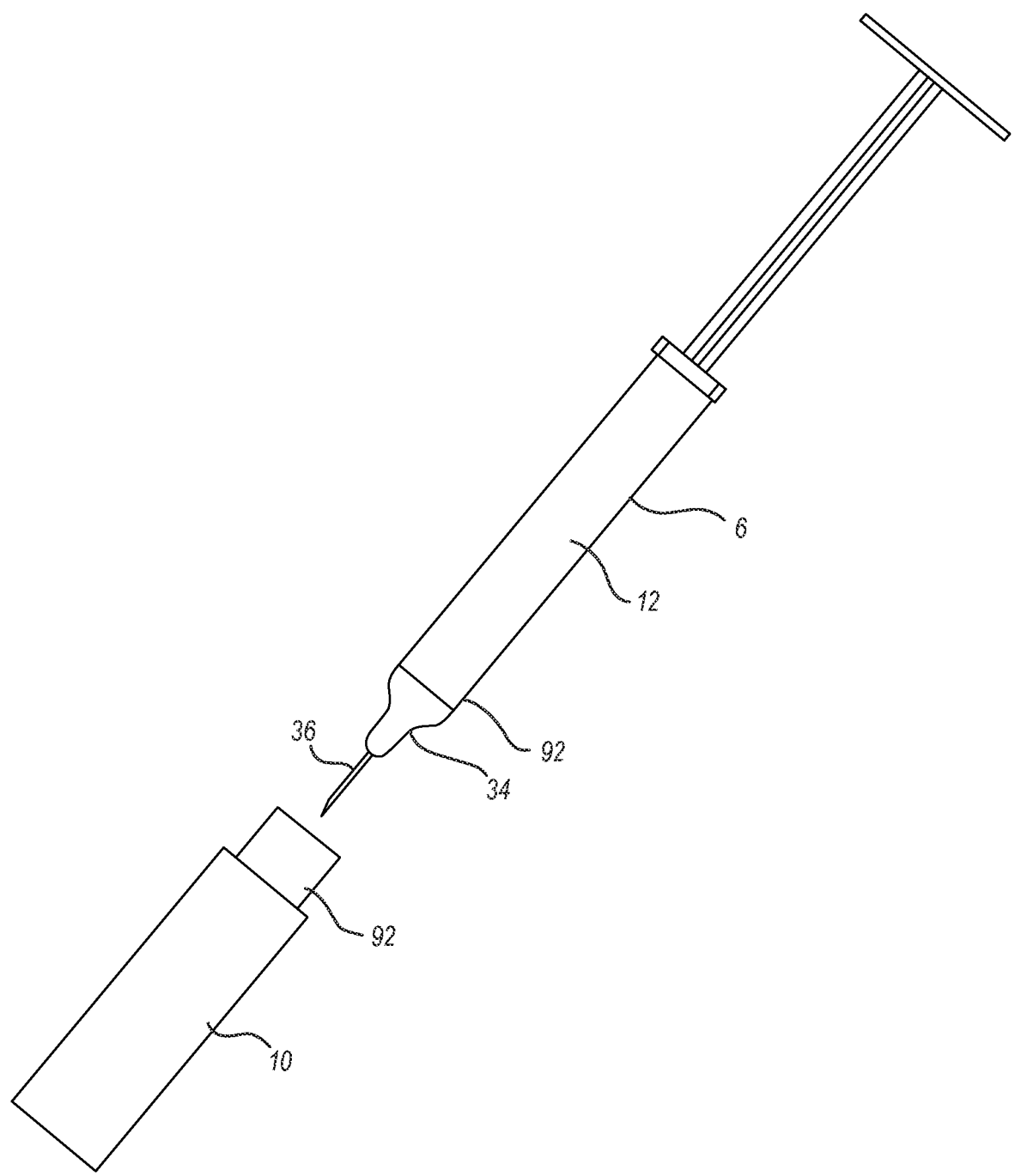
FIG. 11A is a perspective view of the blinding cap housing the rigid needle shield being separated from the syringe shown in FIG. 9 where the optional seal is not used.

It is appreciated that seal 172 is optional and can be eliminated. For example, where no seal 172 is used and it is desired to administer the dosage within syringe 6, blinding cap 10, as shown in FIG. 9 without seal 172 attached, is simply pulled distally relative to syringe 6/syringe barrel 12. In so doing, flange 84 (FIG. 8) again pushes against proximal end face 41 of needle shield 8, thereby causing needle shield 8 and blinding cap 10 to concurrently pull off of syringe barrel 12 and needle 36, as now depicted in FIG. 11A. Again, flange 84 (FIG. 8) not only assists in helping to concurrently remove needle shield 8 with blinding cap 10 but, once needle shield 8 and blinding cap 10 have been removed as depicted in FIG. 11A, flange 84 continues to assist in covering and obscuring needle shield 8 within blinding cap 10, thereby further limiting the ability to detect any discernable features of needle shield 8.

It is appreciated that blinding cap 10 can have a variety of different configurations. For example, it is not necessary that body 90 and sleeve 92 have a cylindrical configuration. In alternative embodiments, each could have a transverse cross section that is elliptical, oval, polygonal or have other configurations. Furthermore, in the above discussed embodiment, with reference to FIG. 8, flange 84 is received within slot 170. In one alternative, needle shield 8 can have an outer diameter that is larger than the outer diameter of syringe barrel 12. In this case, flange 84 can still be disposed proximally of proximal end face 41 of needle shield 8 for pushing against proximal end face 41 without being received within slot 170. As such, the present invention does not always require that flange 84 be received within slot 170.

Figure 12:
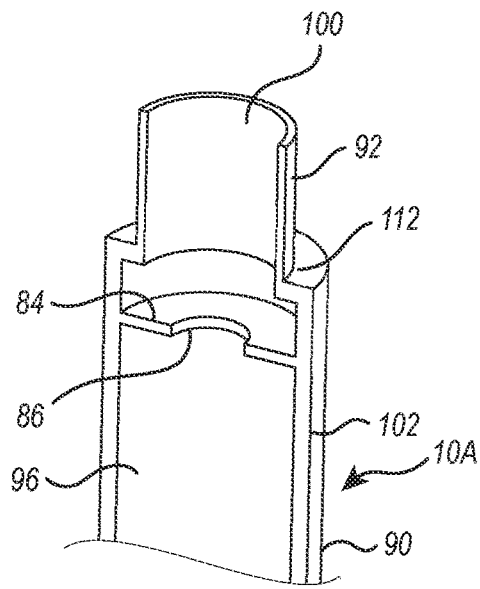
FIG. 12 is a perspective view of a first alternative embodiment of the blinding cap shown in FIG. 1 where the flange projects from the sidewall of the body.

Depicted in FIG. 12 is another alternative embodiment of a blinding cap 10A where like elements between blinding caps 10 and 10A are identified by like reference characters. Blinding cap 10A is the same as blinding cap 10 except that rather than flange 84 inwardly projecting from proximal end wall 112, flange 84 radially inwardly projects from sidewall 102 at a location distal of proximal end wall 112. In this configuration, needle shield 8 is received within the portion of chamber 96 distal of flange 84 while the distal end of syringe barrel 12 extends through both the portion of chamber 96 proximal of flange 84 and through channel 100 of sleeve 92. Again in this embodiment, flange 84 is positioned proximal of proximal end face 41 of needle shield 8, such as within slot 170, so that flange 84 will press against proximal end face 41 when blinding cap 10A is moved distally relative to syringe 6/syringe barrel 12.

Figure 13:
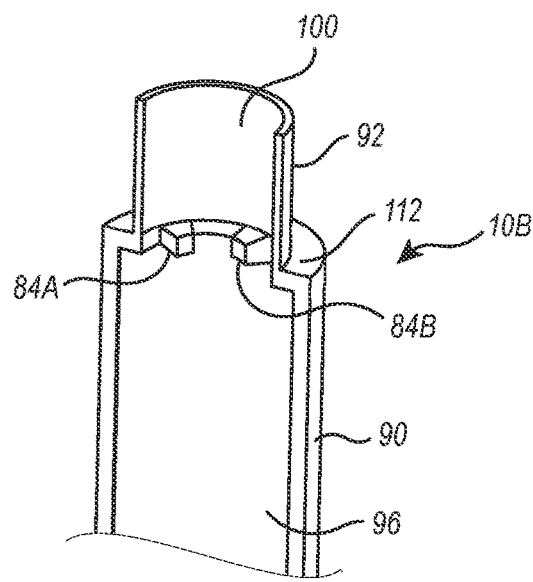
FIG. 13 is perspective view of a second alternative embodiment of the blinding cap shown in FIG. 1 comprising a plurality of radially spaced apart flanges.

Depicted in FIG. 13 is another alternative embodiment of a blinding cap 10B where like elements between blinding caps 10 and 10B are identified by like reference characters. Blinding cap 10B is the same as blinding cap 10 except that rather than having a single annular flange 84 that radially inwardly projects from proximal end wall 112, flange 84 is replaced within a plurality of radially spaced apart, non-annular flanges that radially inwardly project from proximal end wall 112. In this depicted embodiment, flanges 84A and 84B are shown. In other embodiments, a single flange 84A can be used. In yet other embodiments, at least or less than 2, 3, 4, 6, or 8, non-annular flanges can be used. Again, during use, flanges 84A and 84B, or whatever number of flanges are used, are positioned proximal of proximal end face 41 of needle shield 8, such as within slot 170, so that flanges 84A and 84B will press against proximal end face 41 when blinding cap 10A is moved distally relative to syringe 6/syringe barrel 12. It is noted that flange 84 of blinding cap 10A could also be replaced with the 1, 2, or more of the non-annular flanges of blinding cap 10B.

Figure 14:
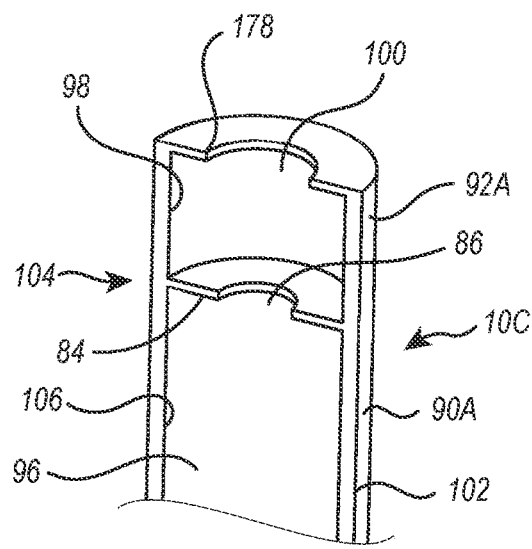
FIG. 14 is a perspective view of a third alternative embodiment of the blinding cap shown in FIG. 1 wherein the sleeve of the blinding cap has the same diameter as the body.

Depicted in FIG. 14 is another alternative embodiment of a blinding cap 10C where like elements between blinding caps 10 and 10C are identified by like reference characters. Blinding cap 10C includes a body 90A that is the same as body 90 except that proximal end wall 112 has been eliminated. Furthermore, sleeve 92 has been replaced with sleeve 92A which has the same outer diameter as body 90A. As such, sleeve 92A extends proximally from sidewall 102 of body 90A. In this embodiment, flange 84 radially inwardly projects from interior surface 106 of sidewall 102 at proximal end 104 of body 90A. Because sleeve 92A has a larger outer diameter than sleeve 92, an annular flange 178 can be formed that radially inwardly projects from interior surface 98 of sleeve 92A, such as at the proximal end of sleeve 92A. During use, flange 178 would extend inward toward syringe barrel 12 to help prevent visual inspection behind sleeve 92A. In other embodiments, flange 178 can be eliminated. Again, during use, needle shield 8 is received within chamber 96 and flange 84 is positioned proximal of proximal end face 41 of needle shield 8, such as within slot 170, so that flange 84 will press against proximal end face 41 when blinding cap 10A is moved distally relative to syringe 6/syringe barrel 12.

Because sleeve 92A of blinding cap 10C will step out from syringe barrel 12 during use, a different configuration and placement of a seal can be used, if desired. For example, in contrast to using seal 172 (FIG. 10) that circumferentially wraps around syringe barrel 12 and sleeve 92, a seal having an adhesive on one side could be placed that extends longitudinally between syringe barrel 12 and sleeve 92A, i.e., one end attaches to syringe barrel 12 and the opposing end attaches to sleeve 92A. A perforation line could be formed laterally across this seal and is placed at the intersection between syringe barrel 12 and sleeve 92A.

Figure 15:
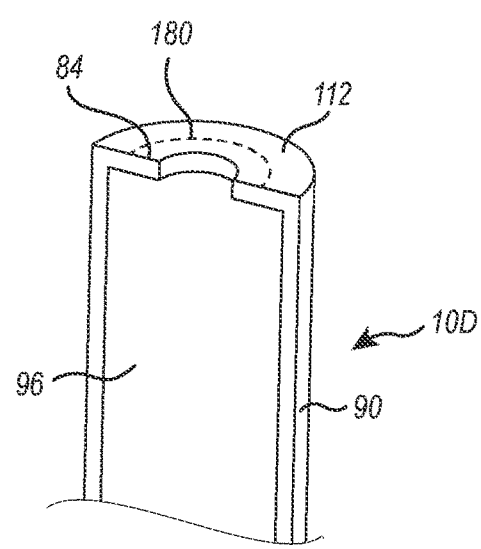
FIG. 15 is a perspective view of a fourth alternative embodiment of the blinding cap shown in FIG. 1 wherein the sleeve is removed from the body.

Depicted in FIG. 15 is another alternative embodiment of a blinding cap 10D where like elements between blinding caps 10 and 10D are identified by like reference characters. Blinding cap 10D is the same as blinding cap 10 except that sleeve 92 has been eliminated. Body 90 can still be described as comprising proximal end wall 112 having flange 84 radially inwardly projecting therefrom. The boundary between proximal end wall 112 and flange 84 is shown by dashed line 180. Alternatively, blinding cap 10D can simply comprise body 90A, discussed with blinding cap 10C, where proximal end wall 112 is eliminated and flange 84 simply radially inwardly projects from interior surface 106 of sidewall 102 at proximal end 104 of body 90A. Again, during use, needle shield 8 is received within chamber 96 and flange 84 is positioned proximal of proximal end face 41 of needle shield 8, such as within slot 170, so that flange 84 will press against proximal end face 41 when blinding cap 10A is moved distally relative to syringe 6/syringe barrel 12. In each of the embodiments discuss herein where annular flange 84 is used, it is appreciated that annular flange 84 can be replaced with 1, 2, or more separate, spaced apart flanges such as flanges 84A and 84B in FIG. 13. Because sleeve 92 has been eliminated from blinding cap 10D, it may also be desirable to eliminate the use of seal 172 (FIG. 10) which typically attaches to sleeve 92. Alternatively, the seal discussed above with regard to blinding cap 10C could be used so as to extend between syringe barrel 12 and body 90.

Figure 16:
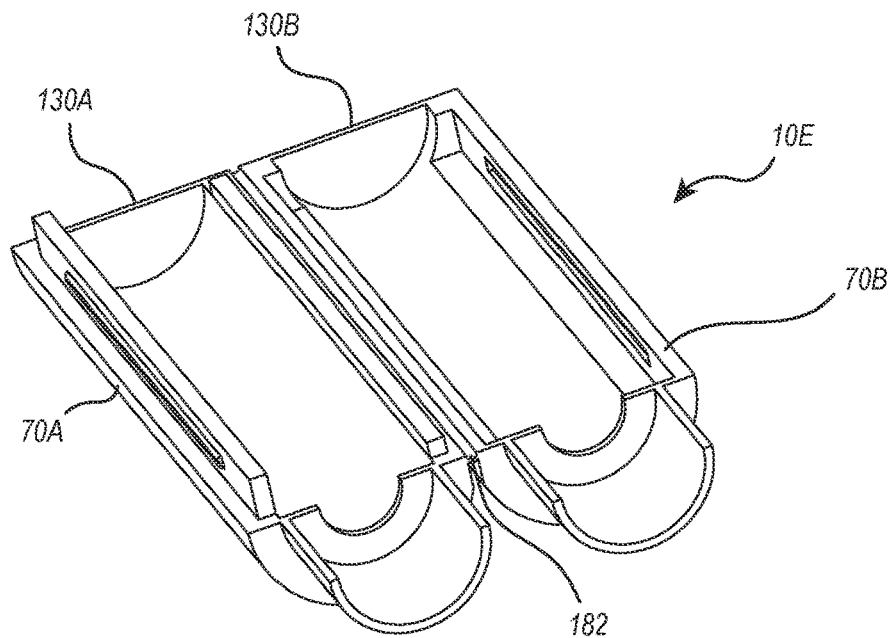
FIG. 16 is a perspective view of a fifth alternative embodiment of the blinding cap shown in FIG. 1 wherein the cap portions of the blinding cap are coupled together by a hinge.
Figure 17:
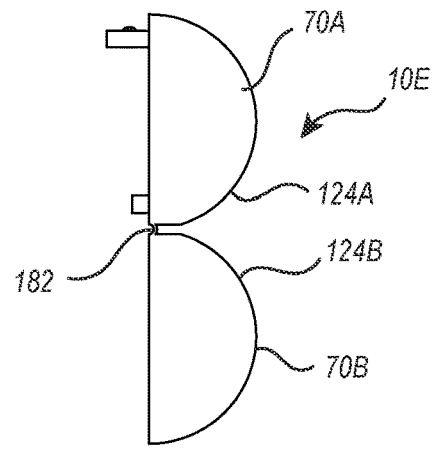
FIG. 17 is an elevated distal end view of the blinding cap shown in FIG. 16.

Depicted in FIGS. 16 and 17 is another alternative embodiment of a blinding cap where like elements between blinding caps 10 and 10E are identified by like reference characters. Blinding cap 10E is the same as blinding cap 10, as discussed with regard to FIG. 6, except that in contrast to cap portions 70A and 70B being two separate discrete members that are coupled together during use, in blinding cap 10E, cap portions 70A and 70B are connected together by a hinge 182. Hinge 182 extends between first sidewall portion 124A of cap portion 70A and second sidewall portion 124B of cap portion 70B. Blinding cap 10E can be moved to its closed position by simply rotating cap portion 70A and/or cap portion 70B about hinge 182. Blinding cap 10E is used in the same was as previously discussed with blinding cap 10. Furthermore, all of the previously discussed means for securing together cap portions 70A and 70B and all of the alternatives previously discussed with regard to blinding cap 10 are also applicable to blinding cap 10E.

Hinge 182 is depicted as a living hinge that is concurrently molded with cap portions 70A and 70B so that cap portions 70A and 70B and hinge 182 form a single, continuous, unitary member as opposed to separate member that are connected together. However, in other embodiments alternative hinge configurations can be used. Furthermore, in the depicted embodiment, hinge 182 is a single hinge that extends along the length of first sidewall portion 124A and second sidewall portion 124B.

Figure 19:
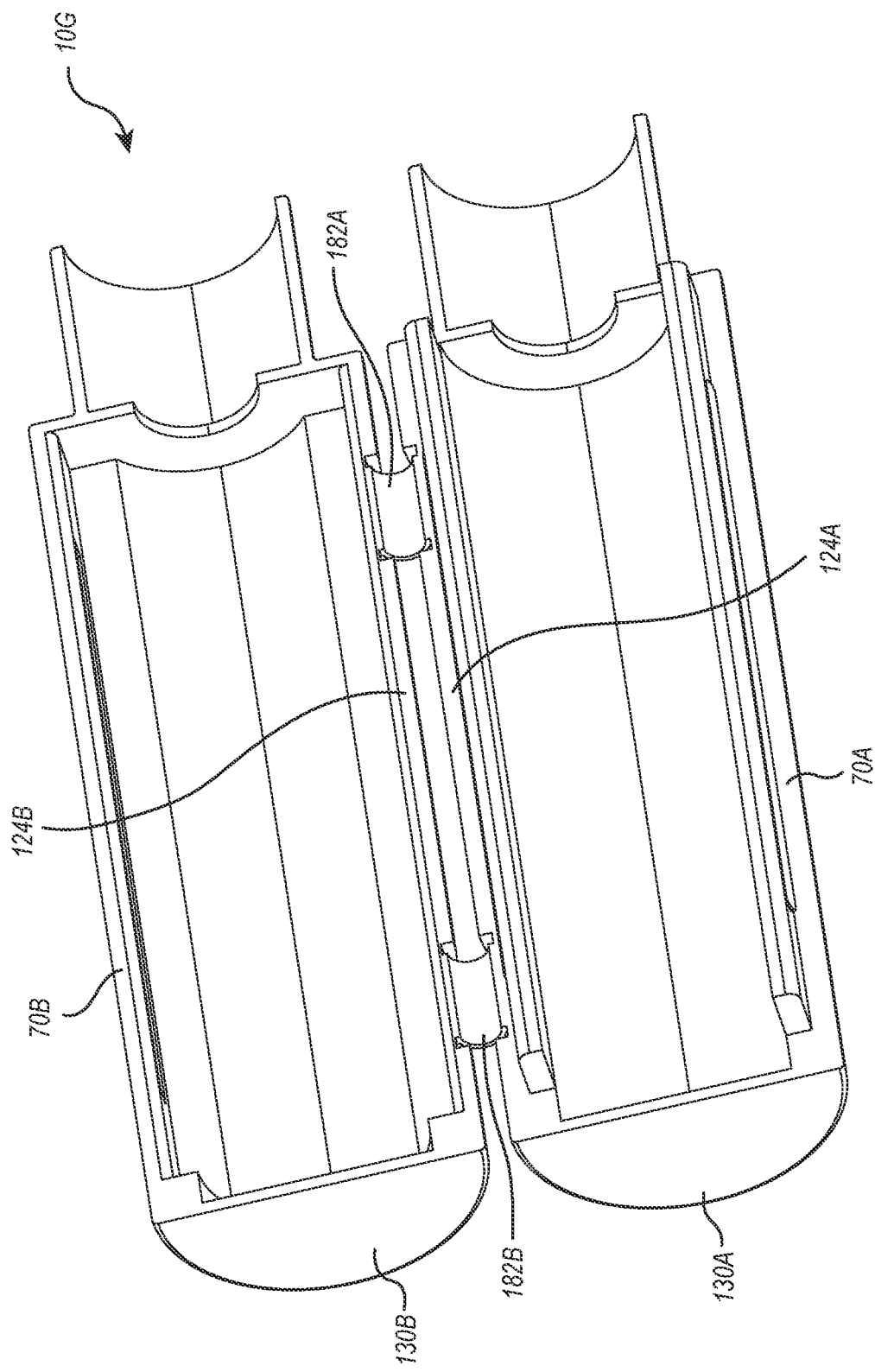
FIG. 19 is a perspective view of another alternative embodiment of the blinding cap shown in FIG. 16 where two spaced apart hinges are used to couple together the cap portions.

In an alternative embodiment, two or more spaced apart hinges can be formed along first sidewall portion 124A and second sidewall portion 124B. For example, depicted in FIG. 19 is a further alternative embodiment of a blinding cap 10G where like elements between blinding caps 10, 10E and 10G are identified by like reference characters. Blinding caps 10E and 10G are substantially the same except that in contrast to having a single hinge 182 extending between cap portions 70A and 70B, blinding cap 10G has two spaced apart hinges 182A and 182B extending between cap portions 70A and 70B. As with hinge 182, hinges 182A and 182B can comprise living hinges that are formed as a single, continuous, unitary member with cap portions 70A and 70B. Alternatively, hinges 182A and 182B can comprise multi-part hinges that mechanically connect together cap portions 70A and 70B. Blinding cap 10G can be moved to its closed position by simply rotating cap portion 70A and/or cap portion 70B about hinges 182A and 182B and is used in the same was as previously discussed with blinding cap 10.

In a further alternative embodiment, in contrast to forming hinge 182 or hinges 182A and 182B between first sidewall portion 124A and second sidewall portion 124B, hinge 182 or hinges 182A and 182B could also be formed between first distal end wall portion 130A and second distal end wall portion 130B.

Figure 18:
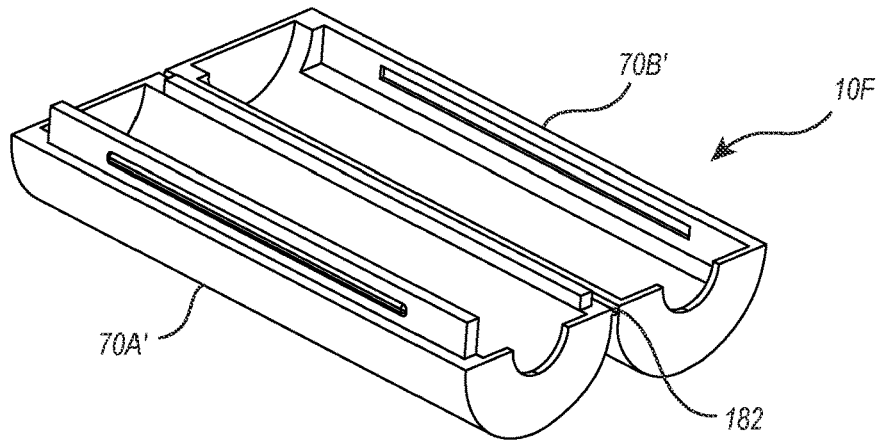
FIG. 18 is a perspective view of an alternative embodiment of the blinding cap shown in FIG. 16 wherein the sleeve portions have been removed.

Finally, depicted in FIG. 18 is another alternative embodiment of a blinding cap 10F where like elements between blinding caps 10, 10E and 10F are identified by like reference characters. Blinding cap 10F is the same as blinding cap 10E including the use of hinge 182, except that sleeve 92 has been eliminated. More specifically, blinding cap 10F includes cap portions 70A' and 70B' that are connected together by hinge 182. Cap portions 70A' and 70B' are the same as cap portions 70A and 70B, respectively, except that first sleeve portion 134A and second sleeve portion 134B have been eliminated. All of the alternatives discussed above with regard to blinding caps 10 and 10E are also applicable to blinding cap 10F.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A blinding cap for covering a needle shield that is covering a needle of a syringe, the blinding cap comprising:
    an elongated body extending between a proximal end and an opposing distal end, the body at least partially bounding a chamber;
    an annular sleeve projecting from the proximal end of the body and at least partially bounding a channel; and
    a first flange comprising a continuous annular ring that radially inwardly projects from the body into the chamber, the first flange encircling an opening that provides communication between the chamber and the channel.

2. The blinding cap as recited in claim 1, wherein the first flange is configured so that when the blinding cap covers a needle shield that covers a needle, the flange is disposed proximally behind a proximal end face of the needle shield for use in removing the needle shield from off the needle.

3. The blinding cap as recited in claim 1, wherein the chamber is completely enclosed except for the opening that communicates with the channel.

4. The blinding cap as recited in claim 1, wherein the chamber and the channel share a common central longitudinal axis.

5. The blinding cap as recited in claim 1, wherein the chamber of the body has a diameter and the channel of the sleeve has a diameter, the diameter of the chamber being larger than the diameter of the channel.

6. The blinding cap as recited in claim 1, wherein the body and the sleeve are opaque.

7. The blinding cap as recited in claim 1, further comprising:
    a first cap portion comprising:
        a first body portion having an interior surface and an opposing exterior surface that extend between a proximal end and an opposing distal; and
        a first sleeve portion projecting from the proximal end of the first body portion and having an interior surface and an opposing exterior surface;
    a second cap portion comprising:
        a second body portion having an interior surface and an opposing exterior surface that extend between a proximal end and an opposing distal end; and
        a second sleeve portion projecting from the proximal end of the second body portion and having an interior surface and an opposing exterior surface;
    means for securely coupling together the first cap portion and the second cap portion,
    wherein when the first cap portion is coupled with the second cap portion by the means for coupling, the first body portion and the second body portion combine to form the body and the first sleeve portion and the second sleeve portion combine to form the sleeve.

8. The blinding cap as recited in claim 7, wherein the means for securely coupling together the first cap portion and the second cap portion comprises a projection extending from first cap portion and a recess formed on the second cap portion, the recess being configured to receive the projection so as to secure the first cap portion to the second cap portion.

9. A blinding cap configured to cover a needle shield that receives a needle of a syringe, the blinding cap comprising:
    an elongated body extending between a first end opposite a second end, the body defining a chamber;
    a sleeve projecting from the first end of the elongated body, the sleeve defining a channel; and
    a flange positioned in the elongated body, the flange projecting inwardly from the chamber and defining an opening that connects the chamber and the channel, the flange extending entirely around the opening.

10. The blinding cap of claim 9, wherein the flange defines an end wall of the elongated body.

11. The blinding cap of claim 9, wherein the flange is spaced from an end wall of the elongated body, the sleeve being connected to the end wall.

12. The blinding cap of claim 9, wherein the flange defines a plurality of radial fingers projecting into the opening.

13. The blinding cap of claim 9, wherein the blinding cap is configured to receive the needle shield in the chamber, and the sleeve is configured to receive a portion of a syringe barrel.

14. The blinding cap of claim 9, wherein the elongated body defines a first body portion and a second body portion, the first body portion defining a first portion of the chamber and the second body portion defining a second portion of the chamber, the first body portion and the second body portion are configured to fasten together to define the chamber.

15. The blinding cap of claim 14, wherein the first body portion defines a slot, and the second body portion defines a projection, the projection is configured to be received by the slot to fasten together the first body portion and the second body portion.

16. The blinding cap of claim 14, wherein the first body portion includes a rib defining a detent, the second body portion includes a slot including a recess, the slot is configured to receive the rib, and the recess is configured to receive the detent to fasten together the first body portion and the second body portion.

17. The blinding cap of claim 14, further comprising a hinge connecting the first body portion and the second body portion.

18. The blinding cap of claim 17, wherein the hinge includes a plurality of hinge members.

19. The blinding cap of claim 9, further comprising a seal member, the seal member partially fastened to the sleeve and partially fastened to a syringe barrel configured to be received by the sleeve.

20. A blinding cap comprising:
a body extending between a first end opposite a second end, the body defining a chamber configured to receive a needle shield, the needle shield configured to receive a needle of a syringe;
a flange defined by the body, the flange defining an opening, the flange extends continuously around the opening, the opening has a diameter that is less than a diameter of the chamber,
wherein the flange is configured to restrict withdrawal of the needle shield from the chamber in response to withdrawal of the needle of the syringe from the needle shield.

21. The blinding cap of claim 20, wherein the flange is spaced from the first end and the second end of the body, the first end of the body includes an aperture, wherein the aperture is larger than the opening.

22. The blinding cap of claim 20, further comprising a sleeve projecting from the first end of the body, the sleeve defining a channel, the flange separates the channel and the chamber.

23. A blinding cap comprising:
a body extending between a first end opposite a second end, the body defining a chamber, the chamber including a first chamber portion and a second chamber portion; and
a flange defined by the body, the flange projecting inwardly from the body and defining an opening, the flange continuously extending around the opening, the flange positioned between the first chamber portion and the second chamber portion, the opening having a diameter less than a diameter of the chamber,
wherein the first chamber portion is configured to receive a needle shield, the needle shield configured to receive a needle of a syringe, and the second chamber portion is configured to receive a portion of the syringe, and
wherein in response to withdrawal of the needle from the needle shield, the flange is configured to restrict withdrawal of the needle shield from the chamber.

24. The blinding cap of claim 23, further comprising:
a sleeve projecting from the first end of the body, the sleeve defining a channel, the channel in communication with the second chamber portion,
wherein in response to the needle shield receiving the needle of the syringe, the channel is configured to receive a portion of the syringe.

* * * * *